United States Patent [19]

Manoury et al.

[11] Patent Number: 4,912,219
[45] Date of Patent: * Mar. 27, 1990

[54] 2-[4-PYRIMIDIN-2-YL AMINO)PIPERIDIN-1-YL]BENZIMIDAZOLE COMPOUND

[75] Inventors: Philippe Manoury, Verrieres le Buisson; Jean Binet, Breuillet; Gerard Defosse, Paris, all of France

[73] Assignee: Synthelabo, Paris, France

[*] Notice: The portion of the term of this patent subsequent to Apr. 11, 2006 has been disclaimed.

[21] Appl. No.: 283,468

[22] Filed: Dec. 12, 1988

Related U.S. Application Data

[63] Continuation of Ser. No. 906,279, Sep. 10, 1986, Pat. No. 4,820,710.

[30] Foreign Application Priority Data

Sep. 11, 1985 [FR] France ................. 85 13453

[51] Int. Cl.4 .......................... C07D 401/14
[52] U.S. Cl. .................................. 544/321
[58] Field of Search ................. 544/321, 331; 514/272

[56] References Cited

U.S. PATENT DOCUMENTS 4,281,005 7/1981 Baldwin et al. ................ 546/113

OTHER PUBLICATIONS

Chemical Abstracts, vol. 107, No. 1, Abstract No. 7211f, p.7212, Jul. 6, 1987.

Primary Examiner—Mary C. Lee
Assistant Examiner—Zinna Nothington-Davis
Attorney, Agent, or Firm—Fleit, Jacobson, Cohn, Price, Holman & Stern

[57] ABSTRACT

Benzimidazole derivatives corresponding to the formula (I)

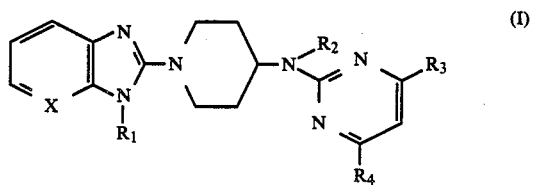

in which
X is CH or N,
R$_1$ is either a hydrogen atom, or a benzyl radical which can bear 1 to 3 substituents chosen from halogen atoms and trifluoromethyl, (C$_{1-4}$)alkyl, (C$_{1-4}$)alkoxy, cyano, methylthio, methylsulphinyl and methylsulphonyl radicals, or a methyl radical bearing a heterocyclic substituent in which the heterocyclic system can be a pyridyl, thienyl or furyl radical and can bear one or more substituents,
R$_2$ is a hydrogen atom or a (C$_{1-4}$)alkyl radical,
R$_3$ is a hydrogen atom or a hydroxy radical, and
R$_4$ is a hydrogen atom or a (C$_{1-4}$)alkyl radical, where appropriate, in tautomeric form when R$_3$ is OH.

The compounds may be used in treating allergy and histamine-induced inflammation.

1 Claim, No Drawings

2-[4-PYRIMIDIN-2-YL AMINO)PIPERIDIN-1-YL]BENZIMIDAZOLE COMPOUND

This is a continuation of application Ser. No. 906,279 filed Sept. 10, 1986, now U.S. Pat. No. 4,820,710.

The present invention relates to benzimidazole derivatives, the preparation thereof and their application in therapy.

The present invention provides compounds of formula (I)

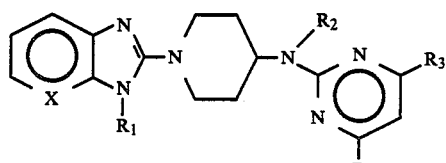

in which X is CH or N;
$R_1$ is hydrogen; unsubstituted benzyl; benzyl substituted by up to 3 substituents chosen from halogen, trifluoromethyl, ($C_{1-4}$) alkyl, ($C_{1-4}$) alkoxy, cyano, methylthio, methylsulphinyl and methylsulphonyl radicals; or heterocyclylmethyl in which the heterocyclic moiety is pyridyl, thienyl or furyl and is unsubstituted or substituted by one or more substituents;
$R_2$ is hydrogen or ($C_{1-4}$) alkyl;
$R_3$ is hydrogen or hydroxy; and
$R_4$ is hydrogen or ($C_{1-4}$) alkyl and tautomers and pharmaceutically acceptable acid addition salts thereof.

Substituents on the heterocyclic moiety when $R_1$ is heterocyclylmethyl are suitably selected from halogen, trifluoromethyl, ($C_{1-4}$)alkyl, ($C_{1-4}$)alkoxy, cyano, methylthio, methylsulphinyl and methylsulphonyl radicals.

Suitable acid addition salts include those of pharmaceutically acceptable organic acids or inorganic acids.

The preferred compounds of the invention are those in which X is CH or N, $R_1$ is a 4-fluorobenzyl radical and $R_2$, $R_3$ and $R_4$ have the meanings given in claim 1.

Among the compounds of the invention in which X is CH, the compounds of choice are those in which $R_1$ is a benzyl radical bearing one or two substituents, and more especially those which bear at the 4-position a single substituent which is a fluorine or chlorine atom or a methyl, methoxy, methylthio, trifluoromethyl, cyano or methylsulphinyl radical.

When $R_3$ is hydroxy and $R_4$ is hydrogen the compounds may exist in several tautomeric forms such as

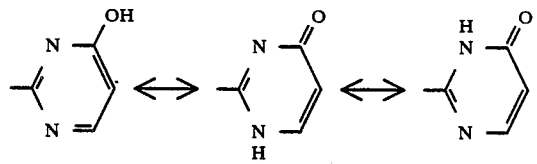

All tautomeric forms of the compounds are part of the invention.

According to the invention, the compounds (I) can be produced by various methods as shown in Schemes I and II:

Scheme 1

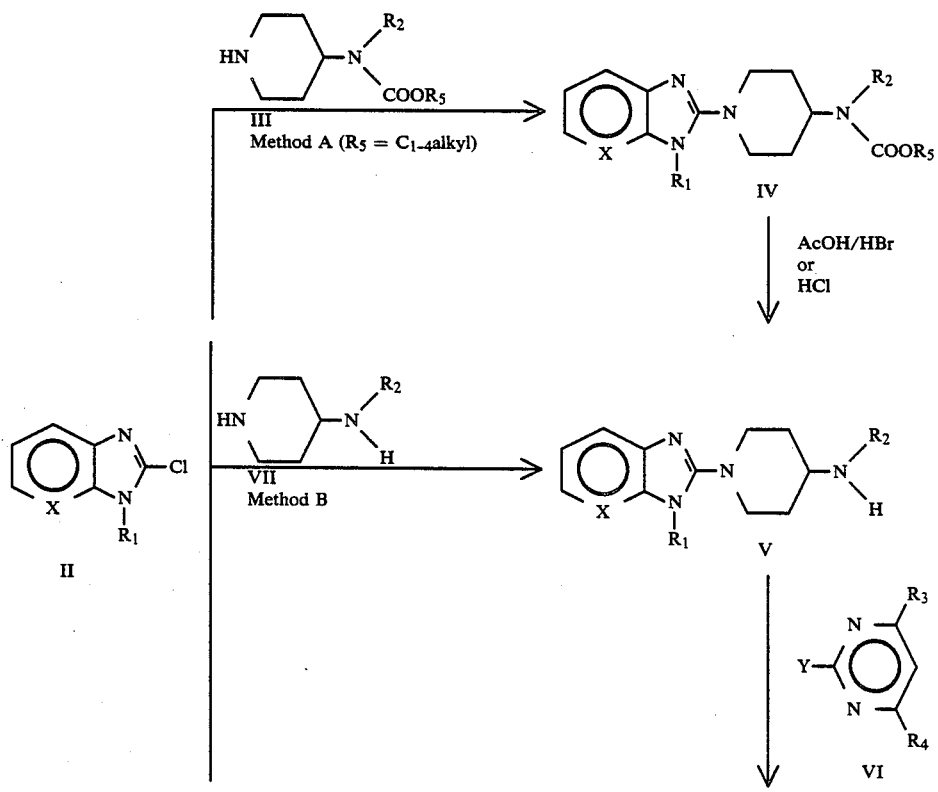

-continued

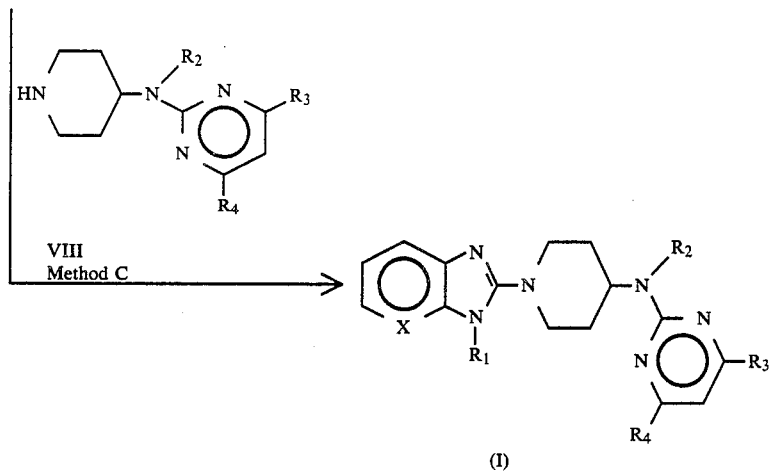

(I)

Scheme 2

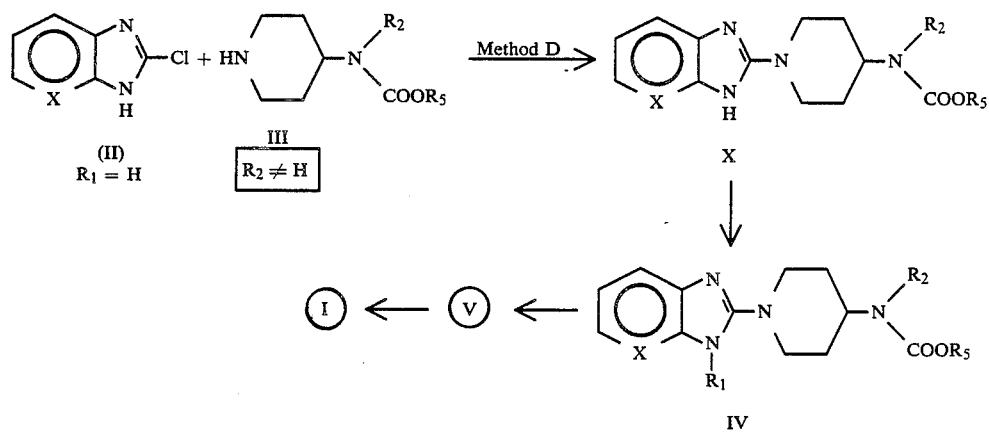

The Methods A, B, C and D are illustrated below by means of examples.

The most general method, method C, is applied to all the compounds, whereas method D is only applicable to the compounds in which $R_2$ is other than hydrogen. Methods A and B are only applicable when $R_1$ is other than hydrogen.

The process of the invention consists in reacting a compound of formula (II) with a 4-[($R_2$)(R) amino]-piperidine of formula

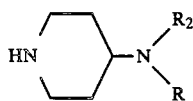

in which $R_2$ is hydrogen or ($C_{1-4}$)alkyl and R denotes either a hydrogen atom,
or a ($C_{1-4}$)alkoxycarbonyl group,
or the group

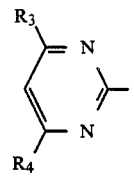

in which $R_3$ is hydrogen or hydroxy, $R_4$ is hydrogen or ($C_{1-4}$)alkyl, and when R is hydrogen, the pyrimidinyl group is introduced in a second stage, whereas when R is a ($C_{1-4}$)alkoxycarbonyl group, this group is removed by hydrolysis and the pyrimidinyl group is then introduced.

According to method A, a compound (II) is condensed with a [($R_2$)(alkoxycarbonyl)amino]piperidine (III) by heating to approximately 150° C., and the compound (IV) obtained is then hydrolysed using hydrobromic acid in acetic acid medium to compound (V) which is reacted with a pyrimidine (VI) in which Y is a leaving group such as methylthio or halogeno especially chloro, bromo or iodo, in the presence or absence of a solvent, at a temperature of 50° to 200° C.

According to method B, a compound (II) is reacted with a [($R_2$)amino]piperidine in the presence of potassium carbonate in an alcoholic solvent, and the compound (V) is condensed with a pyrimidine (VI), in the presence or absence of a solvent, at a temperature of 50° to 200° C.

According to method C, a compound (II) is reacted with a compound (VIII) [obtained by alkylation of a 1-benzyl- or 1-ethoxycarbonyl-4-aminopiperidine with a 2-halo- or 2-alkylthiopyrimidine (VI), followed by catalytic debenzylation or hydrolysis to remove the protective group in the 1-position], in an alcoholic solvent at the reflux temperature.

According to method D, the starting material is a compound (II) in which $R_1$ is hydrogen, and this is condensed with a ($R_2$)(alkoxycarbonyl)amino piperidine (III) by heating to 150° C., the compound obtained (X) is alkylated by the action of an alkyl halide to obtain the compound (IV) which is hydrolysed, and the compound (V) is then condensed with a pyrimidine (VI) as in method A.

The compounds of formulae (II, in which X is CH), (VI) and (VII) are described in the literature; the compounds of formulae (II, in which X is N), (III), (IV), (V) and (VIII, in which $R_3$ is hydroxy) are new.

The compounds of the invention have histamine antagonist activity and can be used for the treatment of allergies such as respiratory allergies, skin allergies and eye allergies, and various allergic manifestations.

Some of the compounds of the invention are very selective for histamine ($H_1$) receptors and are devoid of anticholinergic and antiserotoninergic activity at the therapeutic doses. They possess long-lasting action and their availability when taken orally is very high.

The invention comprises, in consequence, all pharmaceutical compositions containing the compounds and/or their salts as active principles, in combination with all excipients suitable for administering them, especially orally or parenterally.

The administration routes can be the oral and parenteral routes.

The daily dosage can range from 1 to 100 mg.

The examples which follow illustrate the invention. The analyses and the IR and NMR spectra confirm the structure of the compounds.

EXAMPLE 1

2-{[1-{1-[(4-Fluorophenyl)methyl]-1H-benzimidazol-2-yl}-4-piperidyl]methylamino}-4-pyrimidinol (Methods A and B, X=CH, $R_1$=4-F-$C_6H_4$-$CH_2$, $R_2$=$CH_3$, $R_3$=OH, $R_4$=H).

1.1 1-{1-[(4-Fluorophenyl)methyl]-1H-benzimidazol-2-yl}-N-methyl-4-piperidinamine (method A).

1.1.1. 19 g (0.09 mole) of ethyl 4-piperidylcarbamate hydrochloride is solubilized in 120 ml of methanol and neutralized with 17.2 ml of 5.3N sodium methylate. The mixture is filtered and the filtrate evaporated to dryness. The evaporation residue is then mixed with 21.6 g (0.083 mole) of 2-chloro-1-[(4-fluorophenyl)methyl]-1H-benzimidazole and heated to 140° C. for 5 hours. The reaction mass is taken up with methylene chloride and alkalinized with 2N sodium hydroxide. The organic phase is washed with water, dried, filtered and evaporated. The oil obtained is chromatographed on silica (eluent: methylene chloride/methanol, 97.5:2.5). Ethyl[1-{1-[(4-fluorophenyl)-methyl]-1H-benzimidazol-2-yl}-4-piperidyl]carbamate is obtained.

M.p. 136° C.

1.1.2. 21.6 g (0.054 mole) of the compound obtained above, dissolved in 40 ml of dimethylformamide, are added dropwise in the course of approximately half an hour to a suspension, cooled in an icebath, of 3.3 g (0.068 mole) of 50% strength sodium hydride in 40 ml of dimethylformamide. The mixture is allowed to return to room temperature and is agitated for 2 h. It is cooled again using an iced-water bath and 4.7 ml (0.075 mole) of methyl iodide (d=2.28) dissolved in 30 ml of DMF are added. The temperature is allowed to return to 20° C. and the mixture is agitated for 1 h. The reaction mixture is poured into a mixture of water, hexane and isopropyl ether and agitated until crystallization occurs. The precipitate is filtered off and dried. Ethyl[1-{1-[(4-fluorophenyl)methyl]-1H-benzimidazol-2-yl}-4-piperidyl]-N-methylcarbamate is obtained.

M.p. 125° C.

1.1.3. 7 g (0.017 mole) of the compound obtained above, dissolved in 140 ml of acetic acid and 140 ml of 48% strength hydrobromic acid are brought to reflux temperature for 1.5 h. The mixture is evaporated to dryness and the residue taken up with water and alkalinized with 2N sodium hydroxide. Ether is added and the mixture agitated until the product crystallizes. 1-{1-[(4-fluorophenyl)-methyl]-1H-benzimidazol-2-yl}-N-methyl-4-piperidinamine monohydrate is thereby obtained.

M.p. 50° C.

1.2. 1-{1-[(4-Fluorophenyl)methyl]-1H-benzimidazol-2-yl}-N-methyl-4-piperidinamine (method B).

8.7 g (0.05 mole) of 4-methylaminopiperidine (in the form of acetate), 13 g (0.05 mole) of 1-(4-fluorobenzyl)-2-chlorobenzimidazole and 13.8 g (0.1 mole) of potassium carbonate in 250 ml of isoamyl alcohol are brought to reflux temperature for 192 h.

The mixture is cooled and evaporated to dryness. The residue is taken up with a mixture of water and ether and agitated until crystallization occurs. The compound (V) obtained in hydrate form is filtered off. The precipitate is taken up with toluene and agitated until dissolution has occurred, and the solution is dried with magnesium sulphate, filtered and evaporated. The residual oil is ground in petroleum ether. The solid product is filtered off and dried. The compound thereby obtained melts at 77°–80° C.

1.3. 2-{[1-[(4-Fluorophenyl)methyl]-1H-benzimidazol-2-yl-4-piperidyl]methylamino}-4-pyrimidinol.

2.5 g (0.007 mole) of the compound obtained in 1.1. and 1 g (0.007 mole) of methylthiouracil are heated at 170° C. for 10 h. After being cooled, the reaction mass is chromatographed on a silica column (eluent: dichloromethane/methanol, 97:3). The compound obtained is recrystallized in ethanol.

M.p. 217° C.

EXAMPLE 2

1-{1-[(4-Fluorophenyl)methyl]-1H-benzimidazol-2-yl}-N-(2-pyrimidinyl)-4-piperidinamine (Method A, $R_1$=4-F-$C_6H_4$-$CH_2$, $R_2$=$R_3$=$R_4$=H, X=CH).

2.1. 1-{1-[(4-Fluorophenyl)methyl]-1H-benzimidazol-2-yl}-4-piperidinamine.

14.5 g of ethyl [1-{1-[(4-fluorophenyl)methyl]-1H-benzimidazol-2-yl}-4-piperidyl]carbamate dissolved in 250 ml of acetic acid and 250 ml of 48% strength hydrobromic acid are brought to reflux temperature for 2 h. The mixture is evaporated to dryness, the residue taken up with water and alkalinized with 2N sodium hydroxide, and the precipitate filtered off, washed with water and dried. The product is collected in monohydrated form.

2.2. 1-{1-[(4-Fluorophenyl)methyl]-1H-benzimidazol-2-yl}-N-(2-pyrimidinyl)-4-piperidinamine.

A mixture of 1.71 g (0.005 mole) of 1-{1-[(4-fluorophenyl)methyl]-1H-benzimidazol-2-yl}-4-piperidinamine, 0.57 g (0.005 mole) of 2-chloropyrimidine, 0.43 g (0.052 mole) of sodium bicarbonate and 19 ml of ethanol is brought to reflux temperature for 2 days and 2 nights. The mixture is evaporated to dryness, and water and 2N sodium hydroxide are added. The product is taken up with methylene chloride, decanted and washed with water. The product is chromatographed on a silica column (eluent: dichloromethane/methanol, 47:3).

The product obtained is crystallized in ether.
M.p. 190° C.

EXAMPLE 3

2-{[1-{1-(4-Fluorophenyl)methyl]-3H-imidazo-[4,5-b]pyrid-2-yl}-4-piperidyl]methylamino}-4-pyrimidinol (Method C, X=N, $R_1$ =4-F-$C_6H_4$-CH$_2$, $R_2$=CH$_3$, $R_3$=OH, $R_4$=H).

3.1 2-[(4-Piperidyl)(methyl)amino]-1H-pyrimidin-4-one. (Compound VIII).

3.1.1. 2-[(1-Ethoxycarbonyl-4-piperidyl)(methyl)amino]-1H-pyrimidin-4-one.

36 g (0.193 mole) of ethyl 4-methylamino-1-piperidinecarboxylate is placed in the presence of 27.44 g (0.193 mole) of S-methylthiouracil and 730 ml of xylene in a round-bottomed flask placed under a nitrogen circulation system in which the vapor outlet is connected to a system of washing by bleach, and the mixture is heated to the reflux temperature of the solvent for approximately 50 h. The solvent is then evaporated to dryness under vacuum and the solid product obtained is dissolved in refluxing butyl acetate. This solution is filtered hot and the product, which recrystallizes on cooling, is then drained and dried. The compound melts at 177°-179° C.

3.1.2. 2-[(4-Piperidyl)(methyl)amino]1H-pyrimidin-4-one.

A solution of 19.73 g (0.07 mole) of the above compound in 150 ml of 48% strength hydrobromic acid and 150 ml of acetic acid is heated to reflux temperature for 1 h 15 min. The acids are evaporated to dryness in a rotary evaporator. The residue is taken up with a little water and re-evaporated to dryness, this operation being repeated 3 times.

The residue is finally taken up, with cooling, with an excess of concentrated sodium hydroxide solution, and the resulting suspension is then agitated in a sonication bath, cooled in ice and drained. The solid is compressed, washed with a very small amount of ice-cold water and then rinsed copiously with ether. A white solid is obtained.
M.p. 220°-223° C.

3.2. 2-{[1-{1-[(4-Fluorophenyl)methyl]-3H-imidazo[4,5-b]-pyrid-2-yl}-4-piperidyl]methylamino}-4-pyrimidinol.

1.3 g (5×10$^{-3}$ mole) of 2-chloro-1-[(4-fluorophenyl)methyl]-3H-imidazo[4,5-b]pyridine and 1.1 g (5×10$^{-3}$ mole) of 2-[(4-piperidyl)(methyl)amino]-1H-primidin-4-one in 50 ml of 3-methyl-1-butanol are heated to reflux temperature for 5 h. The mixture is left standing overnight and 0.7 g (5×10$^{-3}$ mole) of potassium carbonate is added. The mixture is again brought to reflux temperature for 5 h. It is cooled and evaporated to dryness. The evaporation residue is taken up with water and extracted with ethyl acetate, and the organic phase is washed with water, dried over magnesium sulphate, filtered and evaporated. The product is purified by chromatography on a silica column (eluent: dichloromethane/methanol, 95:5) and the product melting at 185°-187° C. is collected.

EXAMPLE 4

2-{[1-{1-[(4-Cyanophenyl)methyl]-1H-benzimidazol-2-yl}-4-piperidyl]methylamino}-4-pyrimidinol.

4.1. tert-Butyl [1-(1H-benzimidazol-2-yl)-4-piperidyl]-N-methylcarbamate.

32.7 g (0.15 mole) of tert-butyl (4-piperidyl)-N-methylcarbamate and 20.8 g (0.136 mole) of 2-chloro-1H-benzimidazole in 275 ml of 3-methyl-1-butanol are heated to reflux temperature for 4 h 30 min.

The solvent is evaporated off under vacuum and the residue taken up with 20 ml of hot methanol. 28.5 ml of 5.3N sodium methylate are added, and 200 ml of water added. The precipitate formed is drained, washed with water and dried.

A solid melting at 242° C. is obtained.

4.2 tert-Butyl[1-{1-[4-cyanophenyl)methyl]-1H-benzimidazol-2-yl}-4-piperidyl]-N-methylcarbamate.

6.04 g (0.02 mole) of the above product are added in portions to a suspension of 1.14 g (0.0237 mole) of 50% strength NaH in 30 ml of dimethylformamide, and the mixture is agitated for 1 h after the introduction is complete. The mixture is cooled to 0° C. and 4.5 g (0.023 mole) of 4-bromomethylbenzonitrile, dissolved in 15 ml of dimethylformamide, are added. The mixture is agitated for 2 h at 0° C. and then poured into water. The mixture is extracted with ether and the organic phase washed with water, dried, filtered and evaporated. The product is purified by chromatography on a silica column (eluent: dichloromethane/methanol, 98:2). The product melting at 146° C. is obtained.

4.3. 1-{1-[(4-Cyanophenyl)methyl]-1H-benzimidazol-2-yl}-N-methyl-4-piperidinamine.

4.8 g (0.0107 mole) of the above product in 20 ml of 3N hydrochloric acid are heated to 50° C. for 1 h. When hydrolysis is complete, the solution is cooled, alkalinized with 5N sodium hydroxide and extracted with dichloromethane. The product melting at 133° C. is obtained.

4.4 2-{[1-{1-(4-Cyanophenyl)methyl]-1H-benzimidazol-2-yl}-4-piperidyl]methylamino}-4-pyrimidinol.

3.5 g (0.01 mole) of the above product and 1.4 g (0.01 mole) of S-methylthiouracil in 35 ml of toluene are brought to reflux temperature for 168 h. The mixture is cooled and evaporated to dryness and the residue chromatographed on a silica column (eluent: dichloromethane/methanol, 98:2 and then 96:4). The product melting at 198° C. is obtained.

The compounds of the invention which were prepared by way of examples are shown in the table which follows (I).

The intermediate compounds of formula (IV) which are new are shown in the table which follows (II).

TABLE 1

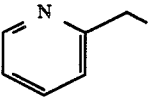

(I)

| N° | X | R₁ | R₂ | R₃ | R₄ | M.p. °C. |
|---|---|---|---|---|---|---|
| 1 | CH | H | $CH_3$ | OH | H | 280 |
| 2 | CH | $C_6H_5-CH_2$ | $CH_3$ | OH | H | 254 |
| 3 | CH | $4-F-C_6H_4-CH_2$ | H | H | H | 190 |
| 4 | CH | $4-F-C_6H_4-CH_2$ | H | OH | H | 244 |
| 5 | CH | $4-F-C_6H_4-CH_2$ | $CH_3$ | OH | H | 217 |
| 6 | CH | $4-F-C_6H_4-CH_2$ | $CH_3$ | OH | $CH_3$ | 241 |
| 7 | CH | $4-F-C_6H_4-CH_2$ | $CH_3$ | OH | $C_3H_7$ | 247 |
| 8 | CH | $4-F-C_6H_4-CH_2$ | $C_2H_5$ | OH | H | 210 |
| 9 | CH | $4-F-C_6H_4-CH_2$ | $C_3H_7$ | OH | H | 201 |
| 10 | CH | $4-CH_3O-C_6H_4-CH_2$ | $CH_3$ | OH | H | 206 |
| 11 | CH | $4-CH_3-C_6H_4-CH_2$ | $CH_3$ | OH | H | 215 |
| 12 | CH | $4-CF_3-C_6H_4-CH_2$ | $CH_3$ | OH | H | 140 |
| 13 | CH | $4-CN-C_6H_4-CH_2$ | $CH_3$ | OH | H | 198 |
| 14 | CH | $4-Cl-C_6H_4-CH_2$ | $CH_3$ | OH | H | 146 |
| 15 | CH | $4-CH_3S-C_6H_4-CH_2$ | $CH_3$ | OH | H | 215 |
| 16 | CH | $4-CH_3SO-C_6H_4-CH_2$ | $CH_3$ | OH | H | 184 |
| 17 | CH | $4-F-3CF_3-C_6H_3-CH_2$ | $CH_3$ | OH | H | 195 |
| 18 | CH | $2,4diF-C_6H_3-CH_2$ | $CH_3$ | OH | H | 213 |
| 19 | CH | (pyridylmethyl) | $CH_3$ | OH | H | 254 |
| 20 | CH | (furylmethyl) | $CH_3$ | OH | H | 160 |
| 21 | N | $4F-C_6H_4-CH_2$ | $CH_3$ | OH | H | 185 |

TABLE II

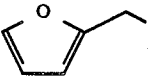

(IV)

| X | R₁ | R₂ | COOR₅ | M.p. °C. |
|---|---|---|---|---|
| CH | H | $CH_3$ | $COOC_2H_5$ | 218 |
| CH | H | $CH_3$ | COOtBu | 237 |
| CH | $4-F-C_6H_4-CH_2$ | $CH_3$ | $COOC_2H_5$ | 125 |
| CH | $4-F-C_6H_4-CH_2$ | $C_2H_5$ | $COOC_2H_5$ | 129 |
| CH | $4-CH_3-C_6H_5-CH_2$ | $CH_3$ | $COOC_2H_5$ | 107 |
| CH | $4-CN-C_6H_4-CH_2$ | $CH_3$ | COOtBu | 146 |
| CH | $4-Cl-C_6H_4-CH_2$ | $CH_3$ | $COOC_2H_5$ | 120 |
| CH | $4-F-3CF_3-C_6H_4-CH_2$ | $CH_3$ | COOtBu | 125 |
| CH | $2,4diF-C_6H_4-CH_2$ | $CH_3$ | COOtBu | 158 |

TABLE II-continued

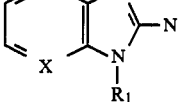

(IV)

| X | R₁ | R₂ | COOR₅ | M.p. °C. |
|---|---|---|---|---|
| CH | (pyridylmethyl) | $CH_3$ | $COOC_2H_5$ | 103 |
| CH | (furylmethyl) | $CH_3$ | COOtBu | 133 |

PHARMACOLOGICAL DATA

The compounds were subjected to various pharmacological trials which mainly showed their antagonistic activity towards histamine and, in some cases, towards serotonin.

1. Activity in vitro: isolated guinea pig ileum

The test was performed according to Magnus' method modified by Savini (Arch. Int. Pharmacodyn., 1957, 113, 157), on male tricoloured guinea pigs weighing approximately 300 g fasted for 18 hours.

A fragment of ileum is removed, placed at 39° C. in a Tyrode bath through which a stream of carbogen (95% $O_2$, 5% $CO_2$) passes, and connected to an isotonic sensor with a maximum tension of 2.5 g. The contractions are recorded using an Ugo Basile microdynamometer.

Contractions are induced by the various spasmogenic agents and the concentration of these which causes a submaximal response is determined (histamine: 1 to $8 \times 10^{-8}$ g/ml.

The compounds of the invention, dissolved in distilled water or a 0.1N solution of methanesulphonic acid, are brought into contact with the ileum for 1 min before the introduction of the spasmogenic substance.

The $AC_{50}$ (concentration which decreases by 50% the contractions induced by histamine) values of the compounds of the invention range from $10^{-7}$ to $10^{-8}$ molar.

2. Activity in vivo: histamine-induced inflammation

Intraplantar injection of histamine (2mg) into one of the hind paws of a rat causes an oedema which is measured, 1 hour after the injection, using an Ugo Basile mercury plethysmometer.

The compounds of the invention, suspended in Tween in 1% strength solution in distilled water, are administered p.o. (0.5 ml/100 g) 1 hour before the injection of the inflammatory agent.

The $AD_{40}$ (dose which decreases by 40% the volume of the oedema) values of the compounds of the invention vary from 0.2 to 10 mg/kg.

When administered orally the compounds have a $LD_{50} > 1000$ mg/kg in acute toxicity tests.

We claim:
1. 2-{[1-{1-[(4-Fluorophenyl)methyl]-1H-benzimidazol-2-yl}-4-piperidyl]methylamino}-4-pyrimidinol.

* * * * *